(12) United States Patent
Park et al.

(10) Patent No.: US 11,237,172 B2
(45) Date of Patent: Feb. 1, 2022

(54) METHOD FOR SCREENING PERSONALIZED INTESTINAL ENVIRONMENT-IMPROVING MATERIAL AND COMPOSITION THEREFOR

(71) Applicant: HEM Inc., Suwon-si (KR)

(72) Inventors: Soyoung Park, Suwon-si (KR); Yosep Ji, Suwon-si (KR)

(73) Assignee: HEM Inc., Suwon-si (KR)

( * ) Notice: Subject to any disclaimer, the term of this patent is extended or adjusted under 35 U.S.C. 154(b) by 0 days.

(21) Appl. No.: 16/932,626

(22) Filed: Jul. 17, 2020

(65) Prior Publication Data

US 2021/0063407 A1 Mar. 4, 2021

Related U.S. Application Data

(63) Continuation-in-part of application No. PCT/KR2020/001485, filed on Jan. 31, 2020.

(30) Foreign Application Priority Data

Aug. 30, 2019 (KR) .......................... 10-2019-0107146

(51) Int. Cl.
| | | |
|---|---|---|
| *G01N 31/00* | (2006.01) | |
| *G01N 33/53* | (2006.01) | |
| *G01N 33/68* | (2006.01) | |
| *G01N 33/50* | (2006.01) | |
| *A61P 1/00* | (2006.01) | |
| *A61B 17/00* | (2006.01) | |

(52) U.S. Cl.
CPC ............ *G01N 33/6815* (2013.01); *A61P 1/00* (2018.01); *G01N 33/5041* (2013.01); *G01N 33/5044* (2013.01); *A61B 2017/00818* (2013.01)

(58) Field of Classification Search
None
See application file for complete search history.

(56) References Cited

FOREIGN PATENT DOCUMENTS

| | | |
|---|---|---|
| JP | 2006288272 A | 10/2006 |
| JP | 2009542245 A | 12/2009 |
| JP | 2015525576 A | 9/2015 |
| KR | 1020150036004 A | 4/2015 |

OTHER PUBLICATIONS

Lau et al. Genome Medicine, vol. 8, No. 72, pp. 1-10 (Year: 2016).*
International Search Report and Written Opinion for International application No. PCT/KR2020/001485, dated May 29, 2020, ISA/KR, 8 pages.
MacFarlane, G. T et al., Influence of mucin on glycosidase, protease and arylamidase activities of human gut bacteria grown in a 3-stage continuous culture system, Journal of Applied Bacteriology, 1989, pp. 407-417, vol. 66.

* cited by examiner

*Primary Examiner* — Lisa V Cook
(74) *Attorney, Agent, or Firm* — Lucas & Mercanti, LLP

(57) ABSTRACT

The present disclosure relates to a composition for screening an intestinal environment-improving material and a screening method using the composition, and according to the composition and the method of the present disclosure, it is possible to provide an effective analysis method for screening a microbiota-improving candidate material in a personalized manner by providing a method for verifying personalized probiotics, prebiotics, foods, health functional foods and drugs under in vitro conditions based on microbiota and microbiota metabolites.

13 Claims, 13 Drawing Sheets

FIG. 1

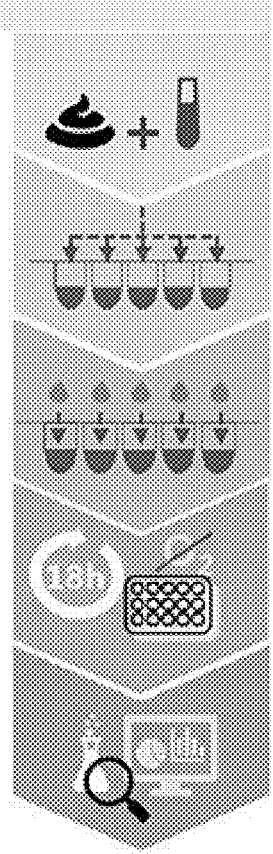

PMAS process

MIX FAECES SAMPLE WITH PMAS MEDIUM AND HOMOGENIZE

DISPENSE SAME AMOUNT OF SAMPLE (REPLICATE INTESTINAL MICROBIOTA IN FAECES)

TREAT DISPENSED SAMPLE WITH CANDIDATE MATERIAL

CULTURE UNDER ANAEROBIC CONDITION FOR PREDETERMINED PERIOD OF TIME

ANALYZE RESULT OF EACH WELL AFTER CULTURING
- gut microbiota (NGS)
- short-chain fatty acids (GC)

COMPARE WHETHER INTESTINAL ENVIRONMENT HAS BEEN IMPROVED AFTER PMAS CULTURING TREATED WITH VARIOUS CANDIDATE MATERIALS
→ SCREENING OF INTESTINAL ENVIRONMENT-IMPROVING CANDIDATE MATERIAL BASED ON INTESTINAL MICROBIOTA IN EACH FAECES

ABX ANTIBIOTIC MIXTURE; CB *Clostridium butyricum* MIYAIRI 588; LB *Lactobacillus* strains; EF *Enterococcus faecium* strain; BF *Bifidobacterium* strains

METHOD FOR SCREENING PERSONALIZED INTESTINAL ENVIRONMENT-IMPROVING MATERIAL AND COMPOSITION THEREFOR

CROSS-REFERENCE TO RELATED APPLICATION

This application is a continuation-in-part of PCT/KR2020/001485 filed Jan. 31, 2020, which claims priority benefit from Korean Patent Application No. 10-2019-0107146, filed Aug. 30, 2019, the entire contents of which are incorporated herein by reference.

FIELD OF THE INVENTION

The present disclosure relates to a composition for screening an intestinal environment-improving material and a screening method using the composition.

BACKGROUND OF THE INVENTION

Genome refers to the gene contained in the chromosome, microbiota refers to the microbial community in the environment as a microbial flora, and microbiome refers to the genome of the total microbial community in the environment. Herein, the microbiome may mean a combination of the genome and the microbiota.

Microbiota is known to play an important role in maintaining the homeostasis of the host, e.g., human immunity, metabolites and the like. The microbiota and the host transmit and receive chemical signals to and from each other, and the expression of immune cells, neurotransmitter production and short-chain fatty acids (SCFA) by the microbiota have a significant effect on the host system.

Probiotics/prebiotics balance the host's unbalanced microbiota so that a healthy metabolite of the microbiota boosts the host's health. Existing probiotics, like generic drugs, give everyone the same dose and similar species.

However, per-human microbiome similarity is less than 50%, and there is increasing recognition and research on the personalization of probiotics.

Therefore, the present disclosure proposes a method for verifying the suitability of the individual microbiota of foods, health functional foods and drugs that promote the regulation and improvement of various microbiota including probiotics or prebiotics in a personalized manner.

SUMMARY OF THE INVENTION

In view of the foregoing, the present disclosure provides a composition for screening an intestinal environment-improving material, a screening method using the composition, and a method for providing information for diagnosing a disease by detection of an intestinal biomarker. However, the problems to be solved by the present disclosure are not limited to the above-described problems. Although not described herein, other problems to be solved by the present disclosure can be clearly understood by a person with ordinary skill in the art from the following descriptions.

A first aspect of the present disclosure provides a composition for screening an intestinal environment-improving material, including L-cysteine.

A second aspect of the present disclosure provides a method for screening an intestinal environment-improving material, including: (a) mixing a composition of the first aspect with a sample obtained from a subject; (b) treating one or more intestinal environment-improving candidate materials in the mixture from the process (a) and culturing; and (c) analyzing the culture from the process (b).

According to examples and embodiments of the present disclosure, it is possible to provide an effective analysis method for screening a microbiota-improving candidate material in a personalized manner by providing a method for verifying personalized probiotics, prebiotics, foods, health functional foods and drugs under in vitro conditions based on microbiota and microbiota metabolites.

This method according to the present disclosure can be applied to a biomarker-based screening system and can quickly verify a personalized candidate material with an effective personalized screening method.

BRIEF DESCRIPTION OF THE DRAWINGS

In the detailed description that follows, embodiments are described as illustrations only since various changes and modifications will become apparent to a person with ordinary skill in the art from the following detailed description. The use of the same reference numbers in different figures indicates similar or identical items.

FIG. 1 is an exemplary diagram illustrating a process for screening personalized probiotics, prebiotics, foods, health functional foods and drugs through the PMAS technique.

DETAILED DESCRIPTION OF THE INVENTION

Figure 2:
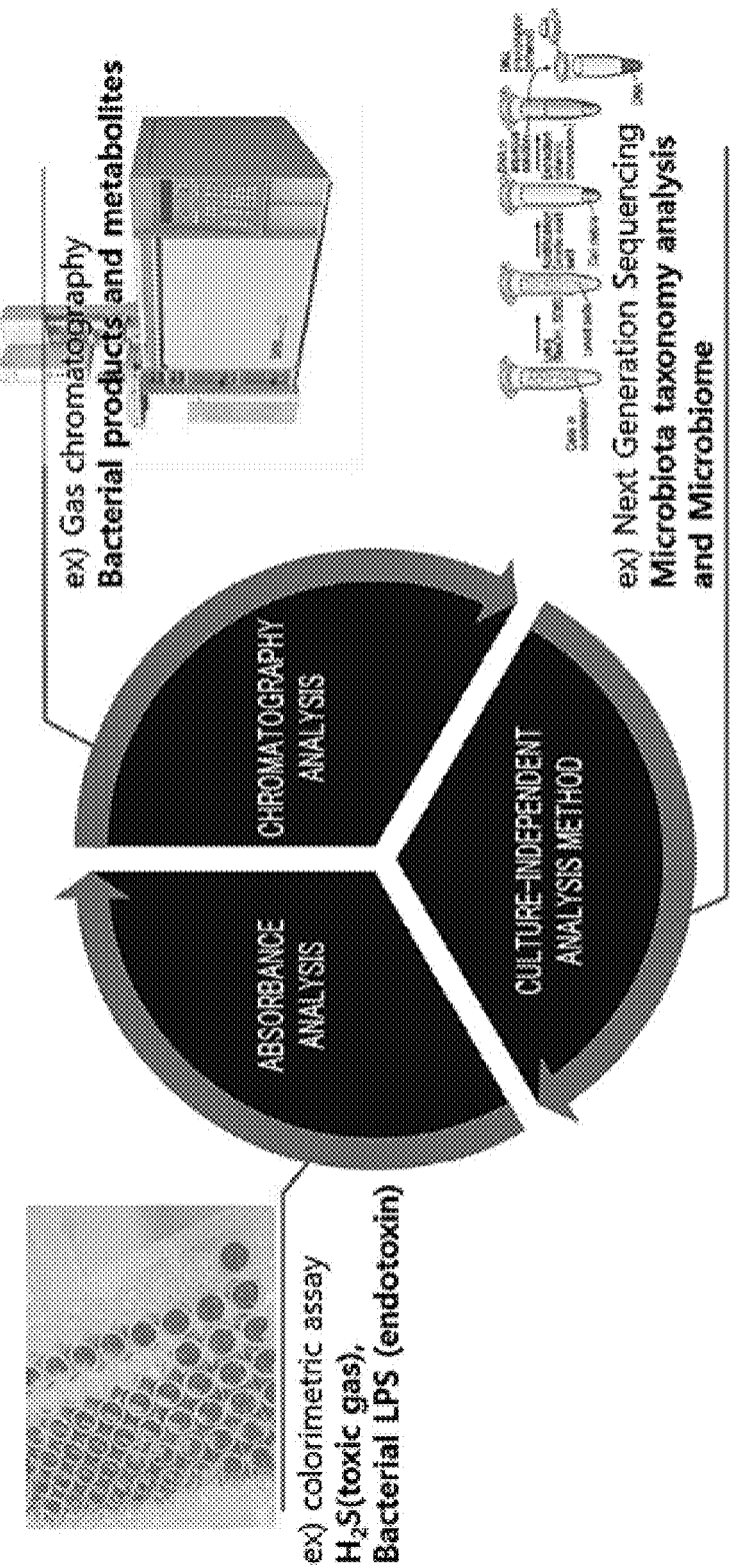
FIG. 2 is an exemplary diagram provided to explain a sample analysis through the PMAS technique.

Through the whole document, the term "comprises or includes" and/or "comprising or including" used in the document means that one or more other components, steps, operation and/or existence or addition of elements are not excluded in addition to the described components, steps, operation and/or elements unless context dictates otherwise.

Through the whole document, the term "about or approximately" or "substantially" is intended to have meanings close to numerical values or ranges specified with an allowable error and intended to prevent accurate or absolute numerical values disclosed for understanding of the present disclosure from being illegally or unfairly used by any unconscionable third party.

Through the whole document, the term "combination(s) of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Through the whole document, a phrase in the form "A and/or B" means "A or B, or A and B".

Hereinafter, embodiments and examples of the present disclosure will be described in detail with reference to the accompanying drawings. However, the present disclosure may not be limited to the following embodiments, examples and drawings.

A first aspect of the present disclosure provides a composition for screening an intestinal environment-improving material, including L-cysteine.

In an embodiment of the present disclosure, the composition is prepared for screening a candidate material capable of improving an intestinal environment. Specifically, it can be understood as a composition to be used in a series of processes of monitoring the progress of improvement in the intestinal environment and evaluating whether the candidate material can improve the intestinal environment, but is not particularly limited thereto.

In an embodiment of the present disclosure, the composition is prepared for identically/similarly mimicking the intestinal environment of an individual user in vitro and makes is possible to accurately and efficiently check whether the candidate material can improve the intestinal environment under in vitro conditions and thus can be usefully used for screening a personalized intestinal environment-improving material.

Through the whole document, the term "intestinal environment improvement" refers to advantageously changing the composition of intestinal microbiota and metabolites of the microbiota. The intestinal environment improvement results in an increase in beneficial intestinal bacteria and metabolites of the beneficial bacteria and thus has effects such as vitamin synthesis, improvement of digestion and absorption, prevention of infection and immunopotentiation, and also results in a decrease in harmful bacteria and metabolites of the harmful bacteria and thus has effects such as decrease in intestinal decomposition, decrease in bacterial toxins and decrease in carcinogens. Also, the intestinal environment improvement can prevent or treat intestinal diseases such as diarrhea, constipation and enteritis and also prevent or treat cancers, obesity, diabetes, and brain-related diseases.

In an embodiment of the present disclosure, the intestinal environment improvement may include one or more selected from the group consisting of an increase in microbial diversity of microbiota, a decrease in endotoxin and hydrogen sulfide derived from intestinal microbiota, an increase in metabolites derived from beneficial microbiota, an increase or decrease in short-chain fatty acids, an increase in kind and number of beneficial bacteria and a decrease in kind and number of harmful bacteria, but may not be limited thereto.

Through the whole document, the term "L-cysteine" is one of amino acid supplements and plays an important role in metabolism as a constituent of glutathione in vivo and is also used to inhibit browning of fruit juices and oxidation of vitamin C.

In an embodiment of the present disclosure, the L-cysteine may be contained at a concentration of from 0.001% (w/v) to 5% (w/v), preferably 0.005% (w/v) to 3% (w/v), more preferably 0.01% (w/v) to 1% (w/v), most preferably from 0.01% (w/v) to 0.1% (w/v), but may not be limited thereto.

In an embodiment of the present disclosure, the L-cysteine may be included in the composition for screening an intestinal environment-improving material in the form of various types of formulations or salts, and specifically, the L-cysteine may be L-cysteine hydrochloride, but may not be limited thereto.

In an embodiment of the present disclosure, the composition may further include mucin, but may not be limited thereto.

Through the whole document, the term "mucin" is a mucosubstance secreted by the mucous membrane and includes submandibular gland mucin and others such as gastric mucosal mucin and small intestine mucin. Mucins are glycoproteins and known as one of energy sources such as carbon sources and nitrogen sources that intestinal microbiota can actually use.

In an embodiment of the present disclosure, the mucin may be contained at a concentration of from 0.01% (w/v) to 5% (w/v), preferably 0.05% (w/v) to 3% (w/v), more preferably 0.07% (w/v) to 2% (w/v), and most preferably from 0.1% (w/v) to 1% (w/v), but may not be limited thereto.

In an embodiment of the present disclosure, the composition may not include any nutrient other than the mucin and specifically may not include a nitrogen source and/or carbon source such as protein and carbohydrate.

In an embodiment of the present disclosure, the protein that serves as a carbon source and nitrogen source may include one or more of tryptone, peptone, and yeast extract, but may not be limited thereto. Specifically, the protein may be tryptone.

In an embodiment of the present disclosure, the carbohydrate that serves as a carbon source may include one or more of monosaccharides such as glucose, fructose and galactose and disaccharides such as maltose and lactose, but may not be limited thereto. Specifically, the carbohydrate may be glucose.

In an embodiment of the present disclosure, the composition may not include glucose and tryptone, but may not be limited thereto.

In an embodiment of the present disclosure, the composition may include one or more selected from the group consisting of sodium chloride (NaCl), sodium carbonate (NaHCO$_3$), potassium chloride (KCl) and hemin. Specifically, the sodium chloride may be contained at a concentration of from 10 mM to 100 mM, the sodium carbonate may be contained at a concentration of from 10 mM to 100 mM, the potassium chloride may be contained at a concentration of from 1 mM to 30 mM, and the hemin may be contained at a concentration of from $1\times10^{-6}$ g/L to $1\times10^{-4}$ g/L, but may not be limited thereto.

In an embodiment of the present disclosure, the composition may be a culture medium composition, but may not be limited thereto.

In an embodiment of the present disclosure, the intestinal environment-improving material may include one or more selected from the group consisting of probiotics, prebiotics, foods, health functional foods and drugs, but may not be limited thereto.

Through the whole document, the term "probiotics" refers to bacteria that exhibit a beneficial in vivo effect on the health of a host. Specifically, probiotics that can reach the intestine and grow in the intestinal mucosa produce lactic acid which acidifies the intestinal environment, and, thus, harmful bacteria that cannot survive in acidic conditions decrease in number and beneficial bacteria that can live well in acidic conditions increase in number, which makes the intestinal environment healthy. The probiotics may include *Lactobacillus, Lactococcus, Enterococcus, Streptococcus, Bifidobacterium* and the like, but may not be limited thereto. The probiotics may be prepared in the form of fermented milk, granules, powder or the like including these strains.

Through the whole document, the term "prebiotics" refers to substances that activate probiotics which are beneficial bacteria thereby inhibiting harmful intestinal bacteria and also create an intestinal environment where probiotics can live well. Also, the prebiotics serve as food to be decomposed and used as energy source for the production of probiotics and are saccharides that cannot be absorbed into the body and thus are not absorbed into the small intestine and reach the intestine where they serve as food for lactic acid bacteria and also cause a decrease in harmful bacteria.

In an embodiment of the present disclosure, the composition may create an intestinal environment under in vitro conditions.

A second aspect of the present disclosure provides a method for screening an intestinal environment-improving material, including: (a) mixing a composition of the first aspect with a sample obtained from a subject; (b) treating one or more intestinal environment-improving candidate materials in the mixture from the process (a) and culturing; and (c) analyzing the culture from the process (b). The features described above in respect of the first aspect of the present disclosure may equally apply to the method according to the second aspect of the present disclosure.

In an embodiment of the present disclosure, the method may be a method for screening a material for preventing and treating diseases caused by intestinal disorders.

In an embodiment of the present disclosure, the method can be understood as a series of processes of treating a sample obtained from a subject in need of intestinal environment improvement with a candidate material capable of improving the intestinal environment, monitoring the progress of improvement in the intestinal environment and evaluating whether the candidate material can improve the intestinal environment, but is not particularly limited thereto. Specifically, if the intestinal environment has been improved when the degree of improvement in the intestinal environment, the candidate material can be determined as an intestinal environment-improving material.

In an embodiment of the present disclosure, the method may be performed under in vitro conditions.

Through the whole document, the term "subject" refers to any living organism which may have an intestinal disorder, may have a disease caused by an intestinal disorder or develop it or may be in need of intestinal environment improvement. Specific examples thereof may include, but not limited to, mammals such as mice, monkeys, cattle, pigs, minipigs, domestic animals and humans, birds, cultured fish, and the like.

Through the whole document, the term "sample" refers to a material derived from the subject and specifically may be cells, urine, feces, or the like, but may not be limited thereto as long as a material, such as microbiota, intestinal microbial metabolites, endotoxins, and short-chain fatty acids, present in the intestine can be detected therefrom.

In an embodiment of the present disclosure, the method may include a process of preparing a sample, a process of pretreating the sample, a process of analyzing the sample and data, and a process of screening a personalized intestinal environment-improving material based on the derived data, but may not be limited thereto.

In an embodiment of the present disclosure, the method may be a fast screening method that is faster than conventionally known microbiota analysis methods and intestinal environment analysis methods. The "fast" may mean specifically 12 hours to 48 hours and more specifically 18 hours to 24 hours, but may not be limited thereto.

In an embodiment of the present disclosure, the culturing in the process (b) may be performed for 12 hours to 48 hours and specifically for 18 hours to 24 hours, but may not be limited thereto.

In an embodiment of the present disclosure, the method may be performed under anaerobic conditions. Specifically, the culturing in the process (b) of the method may be performed under anaerobic conditions.

In an embodiment of the present disclosure, the intestinal environment-improving candidate material may include one or more selected from the group consisting of probiotics, prebiotics, foods, health functional foods and drugs, but may not be limited thereto.

In an embodiment of the present disclosure, the analyzing of the culture in the process (c) is to analyze whether the intestinal environment has been improved or not. Specifically, the analyzing of the culture in the process (c) is to analyze the kind, content and/or concentration of one or more of an endotoxin, hydrogen sulfide as a product of abnormal intestinal fermentation, short-chain fatty acids (SCFAs) and microbiota-derived metabolites contained in the culture and to analyze a change in kind, content and/or concentration when the sample is treated with the candidate material.

Through the whole document, the term "endotoxin" is a toxic substance that can be found inside a bacterial cell and acts as an antigen composed of a complex of proteins, polysaccharides, and lipids.

In an embodiment of the present disclosure, the endotoxin may include lipopolysaccharides (LPS), but may not limited thereto. The LPS may be specifically gram negative and pro-inflammatory.

Through the whole document, the term, "short-chain fatty acid (SCFA)" refers to a short-length fatty acid with six or fewer carbon atoms and is a representative metabolite produced from intestinal microbiota. The SCFA has useful functions in the body, such as an increase in immunity, stabilization of intestinal lymphocytes, a decrease in insulin signaling, and stimulation of sympathetic nerves.

In an embodiment of the present disclosure, the short-chain fatty acids may include one or more selected from the group consisting of formate, acetate, propionate, butyrate, isobutyrate, valerate and iso-valerate, but may not be limited thereto.

In an embodiment of the present disclosure, the analyzing of the culture in the process (c) may be to analyze the kind, content, concentration and/or diversity change of bacteria contained in the microbiota of the culture, but may not be limited thereto.

In an embodiment of the present disclosure, the microbiota may include beneficial intestinal bacteria and harmful intestinal bacteria. Specifically, the beneficial intestinal bacteria may include, but not limited to, *Lactobacillus* and *Bifidobacterium*, and the harmful intestinal bacteria may include, but not limited to, Proteobacteria and *Clostridium difficile*.

In an embodiment of the present disclosure, a method of analyzing the endotoxin, the hydrogen sulfide as a product of abnormal intestinal fermentation, the short-chain fatty acids (SCFAs), the microbiota-derived metabolites, the microbiota, and intestinal microbial diversity may employ various analysis methods, such as genetic analysis methods including absorbance analysis, chromatography analysis and next generation sequencing, and metagenomic analysis methods, that can be used by a person with ordinary skill in the art.

In an embodiment of the present disclosure, the method may further include screening a candidate material that increases the content of the short-chain fatty acids, increases the kind and content of beneficial bacteria in the microbiota, decreases the contents of the endotoxin and the hydrogen sulfide or decreases the kind and content of harmful bacteria in the microbiota by comparison between the result of analysis from the process (c) and the result of analysis on a control group.

Through the whole document, the term "control group" refers to a sample or data without limitation as long as it can be compared in changes of the intestinal environment (kind, concentration and/or content of the short-chain fatty acids, microbiota, endotoxins, hydrogen sulfide and intestinal microbial metabolites) caused by treatment with an intestinal environment-improving candidate material. Specifically, the control group may include a non-treated sample from a subject or a sample treated only with a control material such as vehicle, saline solution, DMSO or the like, but may not be limited thereto.

In an embodiment of the present disclosure, the method includes identically/similarly mimicking the intestinal environment of an individual user including microbiota, temperature, humidity, and motion in vitro and analyzing a predetermined number or more of probiotics, prebiotics, foods, health functional foods and drugs in a parallel manner. Thus, it is possible to rapidly screen the most effective personalized microbiota-improving candidate material.

In an embodiment of the present disclosure, the method may include performing in vitro pretreatment, treatment with a microbiota-improving candidate material, verification of functionality and mode of action of the candidate material to feces samples of human and various animals that can most easily represent the intestinal microbial environment in vivo and examining the taxonomic identification, microbial safety and microbial functionality of the microbiota resulting from the candidate material. As such, through the fast screening method containing an individual's feces and special media and the analysis on feces-derived microbiome and metabolites, it is possible to efficiently screen personalized probiotics, prebiotics, foods, health functional foods and drugs.

In an embodiment of the present disclosure, the method enables screening of personalized probiotics, prebiotics, foods, health functional foods and drugs using samples such as feces. Hereinafter, the method according to the present disclosure will be described as being referred to as Personalized Pharmaceutical Meta-Analysis Screening (PMAS).

A third aspect of the present disclosure provides a method for providing information for diagnosing a disease caused by an intestinal disorder. The features described above in respect of the first aspect and the second aspect of the present disclosure may equally apply to the method according to the third aspect of the present disclosure.

In an embodiment of the present disclosure, the method may include detecting a biomarker for diagnosing a disease caused by an intestinal disorder from the sample obtained from the subject, and the method may include a sample preparation process, a sample pretreatment process, a sample analysis process, a data analysis process, and a process of diagnosing a disease based on the derived data.

In an embodiment of the present disclosure, the biomarker may be a substance detected in the intestine and specifically may include microbiota, endotoxins, hydrogen sulfide, intestinal microbial metabolites, short-chain fatty acids and the like, but may not be limited thereto.

EXAMPLE

Hereinafter, examples of the present disclosure will be described in detail. However, the present disclosure may not be limited thereto.

Example 1. Overall Process of Personalized
Material Candidate Screening System Using
Personalized Pharmaceutical Meta-Analysis
Screening (PMAS) Technique The present disclosure relates to a composition and a method for screening personalized probiotics, foods, health functional foods and drugs under in vitro conditions using samples such as an individual's feces. In the present disclosure, the screening system will be described as being referred to as Personalized Pharmaceutical Meta-Analysis Screening (PMAS).

FIG. 1 is an exemplary diagram illustrating a process for screening personalized probiotics, prebiotics, foods, health functional foods and drugs through the PMAS technique. The overall process of a screening system of the present disclosure will be described below with reference to FIG. 1.

(1) Sample Preparation

Feces of a human or animal and a PMAS medium were mixed at a ratio of 1:12 and homogenized using a stomacher. Then, a filter was used to filter out residues of the feces. Before probiotics, food, health functional food and drug candidate materials were treated, the feces-medium mixture was reduced in an anaerobic chamber for 4 hours.

(2) Dispensing of Feces-Medium Mixture

In the anaerobic chamber, the same amount of the homogenized feces-medium mixture was dispensed to each of culture plates such as 96-well plates.

(3) Material Candidate Treatment

The probiotics, food, health functional food and drug candidate materials to be treated were suspended in sterile 1×PBS to be homogenized in concentration and amount and then dispensed to the respective plates where the feces-medium mixture was placed.

(4) Anaerobic Culture

The plates were cultured under anaerobic conditions with temperature, humidity and motion similar to those of the intestinal environment to ferment and culture the respective test groups.

(5) Sample Analysis

Each of the cultured test groups was centrifuged to separate the supernatant and the pellet. Then, metabolites, short-chain fatty acids, toxic substances and the like from the supernatant were analyzed and microbiota from the pellet were analyzed.

Example 2. Sample Analysis Process Using PMAS Technique

Figure 3:
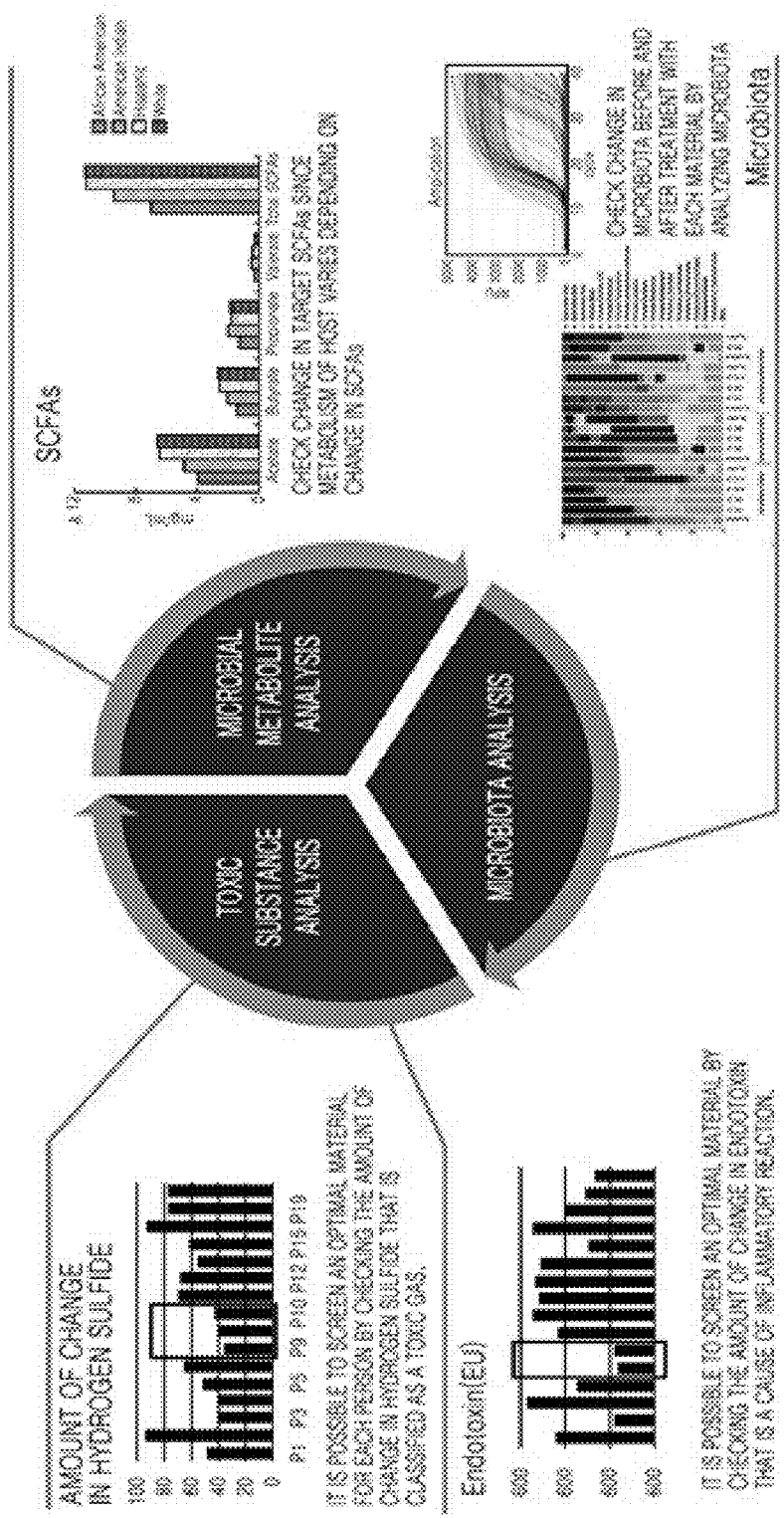
FIG. 3 is an exemplary diagram provided to interpret a sample analysis result through the PMAS technique.

FIG. 2 and FIG. 3 are exemplary diagrams showing the sample analysis process in the PMAS technique of Example 1.

Specifically, after the culture of the test groups treated with the candidate materials is ended, toxic substances such as hydrogen sulfide and bacteria LPS (endotoxins) and microbial metabolites such as short-chain fatty acids from the supernatant obtained by centrifugation of the cultured test groups are analyzed through absorbance analysis and chromatography analysis and a culture-independent analysis method is performed to the microbiota from the centrifuged pellet. For example, the amount of change in hydrogen sulfide produced by the culturing is measured through a methylene blue method using N,N-dimethyl-p-phenylenediamine and iron chloride ($FeCl_3$) and the level of endotoxins that is one of inflammation promoting factors is measured using an endotoxin assay kit. Also, microbial metabolites such as short-chain fatty acids including acetate, propionate and butyrate can be analyzed through gas chromatography. Microbiota can be analyzed by genome-based analysis through metagenomic analysis such as real-time PCR in which all genomes are extracted from a sample and a bacteria-specific primer suggested in the GULDA method or next generation sequencing. That is, the method according to the present disclosure makes it possible to screen a personalized microbiota-improving candidate material based on at least one of analysis on toxic substances, analysis on microbiota-derived metabolites including short-chain fatty acids and analysis on microbiota. Specifically, it is possible to find out a candidate material that decreases in the level of toxic substances through the analysis on toxic substances including endotoxins and hydrogen sulfide, check a change in a predetermined target short-chain fatty acid through the analysis on short-chain fatty acids, and check a change in microbiota before and after the candidate material treatment through the analysis on microbiota. Therefore, it is possible to screen a personalized microbiota-improving candidate material.

Figure 4:
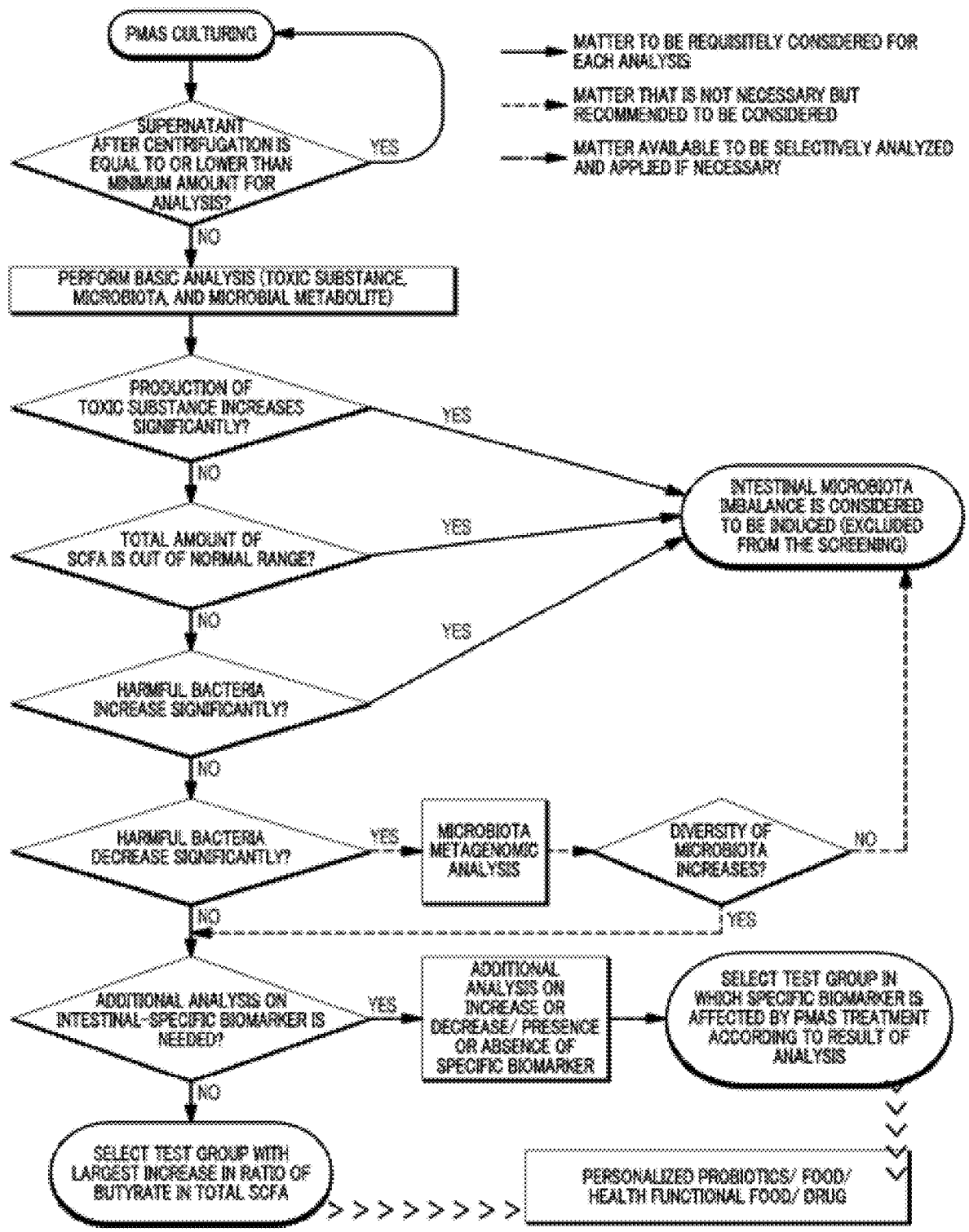
FIG. 4 illustrates an example of screening personalized probiotics, prebiotics, food, health functional food and drug candidate materials based on an analysis result obtained after PMAS.

Example 3. Personalized Material Candidate Screening Process Based on Result of Sample Analysis Using PMAS Technique FIG. 4 is an exemplary diagram showing a process of screening personalized probiotics, foods, health functional foods and drugs based on the result of sample analysis of Example 2.

Specifically, an increase or decrease in the production of toxic substances, a change in SCFA, an increase or decrease in harmful bacteria and beneficial bacteria are determined based on the result of analysis after the execution of PMAS to determine whether the treated candidate material can improve microbiota. If the supernatant does not remain above the minimum amount for analysis when centrifugation is performed after fermentation and culture, the amount of supernatant to be used for analysis is secured by repeating PMAS and culture. If the toxic substances increase and the total amount of short-chain fatty acids is out of the normal range and the harmful bacteria decrease significantly as compared with before the treatment, microbiota imbalance is considered to be induced by the treatment material. Thus, the treatment material is excluded from the screening. However, if the number of beneficial bacteria decreases, it is excluded from the screening only when the diversity of all microbiota examined through metagenomic analysis using next generation sequencing decreases significantly. In addition, to perform screening with reference to the effects of probiotics, food, health functional food and drug candidate materials on a specific intestinal biomarker, analysis on the biomarker is performed for screening only when the candidate materials pass the above-mentioned screening criteria.

That is, the present disclosure makes it possible to screen a personalized microbiota-improving candidate material based on at least one of analysis on toxic substances including endotoxins and hydrogen, analysis on microbiota-derived metabolites including short-chain fatty acids, analysis on harmful intestinal bacteria including Proteobacteria and *Clostridium difficile*, and analysis on beneficial intestinal bacteria including *Lactobacillus* and *Bifidobacterium*. Specifically, it is possible to find out a candidate material that decreases in the level of toxic substances through the analysis on toxic substances including endotoxins and hydrogen sulfide, check a change in a predetermined target short-chain fatty acid through the analysis on short-chain fatty acids, and check an increase or decrease in harmful intestinal bacteria and beneficial intestinal bacteria through the analysis on harmful intestinal bacteria and the analysis on harmful intestinal bacteria. Therefore, it is possible to screen a personalized microbiota-improving candidate material. For example, if the production of toxic substances does not increase significantly, the total amount of short-chain fatty acids is within the normal range, the harmful bacteria do not increase significantly and the beneficial bacteria do not decrease significantly or if the beneficial bacteria decrease significantly but the diversity of microbiota increases, it is possible to select a test group with the largest increase in the ratio of butyrate in the total short-chain fatty acids and perform screening for personalized probiotics, foods, health functional foods and drugs. If the production of toxic substances does not increase significantly, the total amount of short-chain fatty acids is within the normal range, the harmful bacteria do not increase significantly and the beneficial bacteria do not decrease significantly or if the beneficial bacteria decrease significantly but the diversity of microbiota increases and additional analysis on an intestinal-specific biomarker is needed, additional analysis on an increase or decrease and presence or absence of the specific biomarker is performed, and based on the result of analysis, it is possible to select a test group in which the specific biomarker is affected by PMAS treatment and perform screening for personalized probiotics, prebiotics, foods, health functional foods and drugs.

Test Example 1. Checking of Medium Composition for PMAS Technique

To check the optimal composition of a PMAS medium for the PMAS technique of Example 1, a test was performed as follows.

Specifically, feces samples were mixed at a ratio of 1:12 (w/v) with media having various compositions shown in the following Table 1 and then homogenized using a stomacher.

TABLE 1

|  | Test 1 | Test 2 | Test 3 | Test 4 | Test 5 |
|---|---|---|---|---|---|
| Glucose | ◯ | X | ◯ | X | X |
| Tryptone | ◯ | X | X | ◯ | X |

TABLE 1-continued

|  | Test 1 | Test 2 | Test 3 | Test 4 | Test 5 |
|---|---|---|---|---|---|
| Mucin | X | X | X | X | ○ |
| L-cysteine Hydrochloride | X | ○ | ○ | ○ | ○ |

Then, the feces samples were dispensed to 96-well plates. The control group was treated with no material and the prebiotics groups were treated with a prebiotic agent (medium:feces sample:prebiotics=1:12:2 (w/v)) and then cultured under anaerobic conditions at 37° C. for 18 hours. Then, the control group was compared with the prebiotics groups in terms of the contents of butyrate, propionate and acetate.

Figure 5:
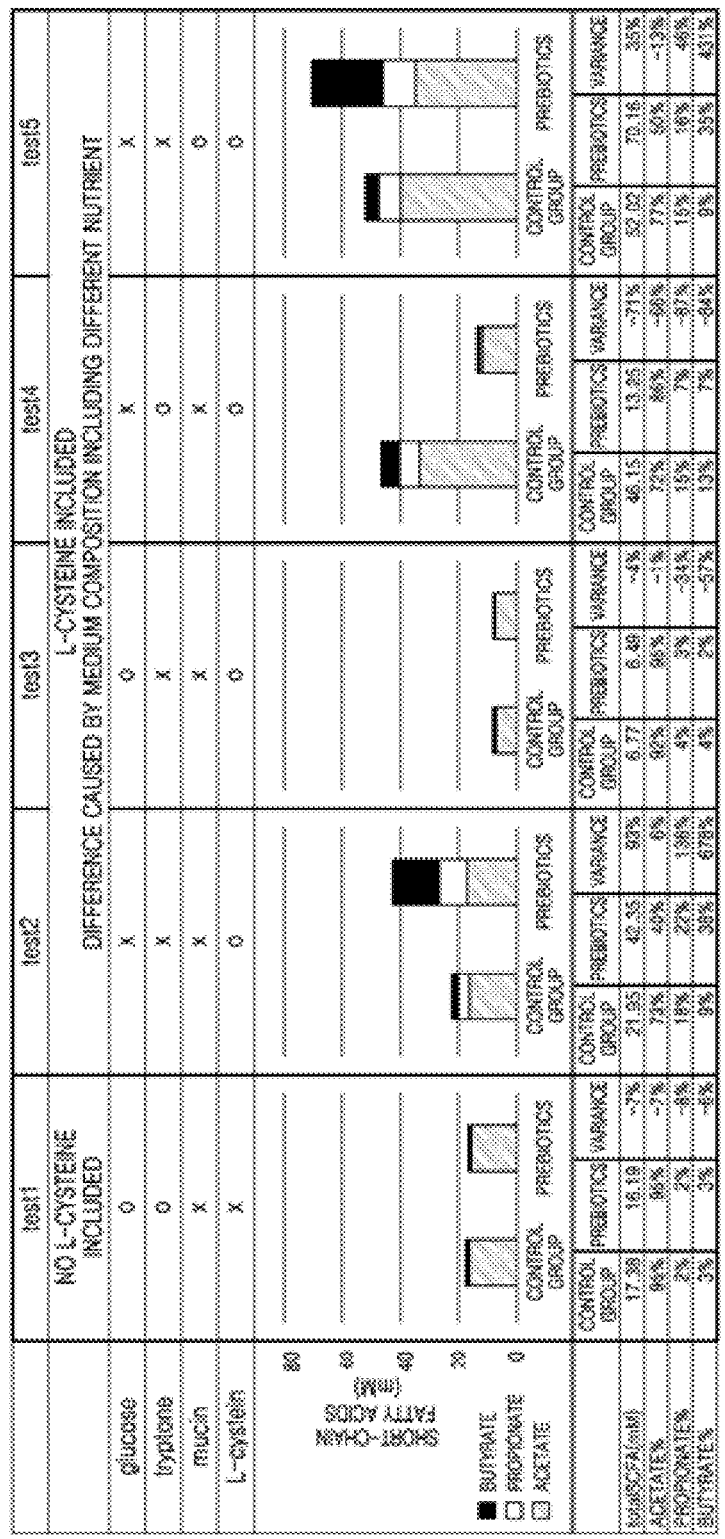
FIG. 5 is a diagram showing an analysis result on the short-chain fatty acid content depending on the composition of a PMAS medium.

As a result, it was verified that Test 1 and Test 3 treated with prebiotics known to be fermented by intestinal microbiota and to produce short-chain fatty acids did not show a change in content of butyrate, propionate and acetate and Test 4 treated with prebiotics showed a decrease in content of butyrate, propionate and acetate (FIG. 5).

On the other hand, it was verified that Test 2 and Test 5 treated with prebiotics showed an overall increase in content of short-chain fatty acids (FIG. 5). Since the absolute amount (mM) of short-chain fatty acids detected was higher in Test 5 than in Test 2, Test 5 is easier to analyze. Therefore, tests to be described in the following Test Examples were performed using media having the composition of Test 5.

According to the above-described results, it can be seen that the composition (Test 2) that contains L-cysteine without nutritive components and the composition (Test 5) that contains L-cysteine and mucin actually showed the predicted results of prebiotics treatment. Therefore, the intestinal environment can be similarly mimicked in vitro with a medium that contains L-cysteine or L-cysteine and mucin without carbohydrate such as glucose and protein such as tryptone, and, thus, it is possible to rapidly and accurately check a change in the intestinal environment caused by treatment with a candidate material.

Test Example 2. Setting of Culture Time for Screening Intestinal Environment-Improving Material To check the optimal culture time for anaerobic culture in the PMAS technique of Example 1, a test was performed as follows.

Specifically, the test was performed in the same manner as in Test Example 1 except that the culture time of anaerobic culture was set to 0 hour, 18 hours, 21 hours, 24 hours, 40 hours and 48 hours. After culturing, the contents of butyrate, propionate and acetate were measured.

Figure 6:
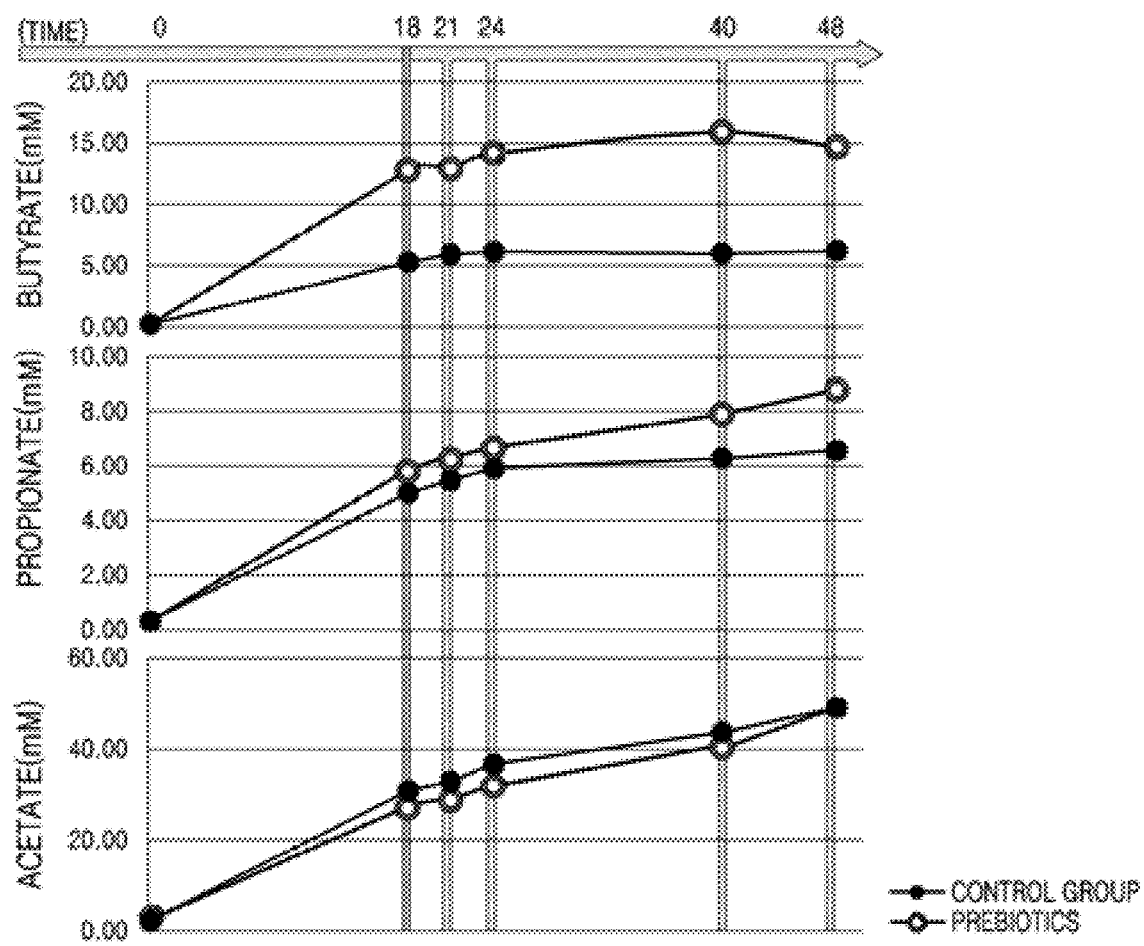
FIG. 6 is a diagram showing an analysis result on the short-chain fatty acid content depending on the PMAS culture time.

As a result, it was verified that both the control group and the prebiotics groups showed a sharp increase in content of short-chain fatty acids up to the culture time of 18 hours and then entered a plateau phase (FIG. 6).

According to the above-described results, it can be seen that when the culture time for anaerobic culture is set to 18 hours, it is the most efficient for fast screening of a candidate material using the PMAS technique of the present disclosure.

Test Example 3. Validation of Personalized Material Candidate Screening Method Using PMAS Technique To verify whether it is possible to accurately screen a personalized candidate material in an individual's intestinal environment created in vitro by using the PMAS technique of the present disclosure, tests were performed as follows.

(1) Verification of Reproducibility

To verify whether the result of analysis using the PMAS technique of the present disclosure is reproduced in the same subject, a test was performed as follows.

Specifically, to verify the reproducibility of PMAS analysis result in feces samples A1 to A4 and B1 to B3 collected on respective dates from different persons A and B, the amount of butyrate was measured from the control group treated with no material and the test groups treated with five candidate materials and the butyrate quantitative values of the test groups treated with five candidate materials were divided by the butyrate quantitative value of the control group to find out the amounts of butyrate increased or decreased when the samples were treated with the materials candidates, respectively. Then, all the results of treatment of the respective samples with the five candidate materials were analyzed using the Pearson correlation (as the correlation coefficient gets closer to 1, it indicates a higher similarity).

Figure 7:
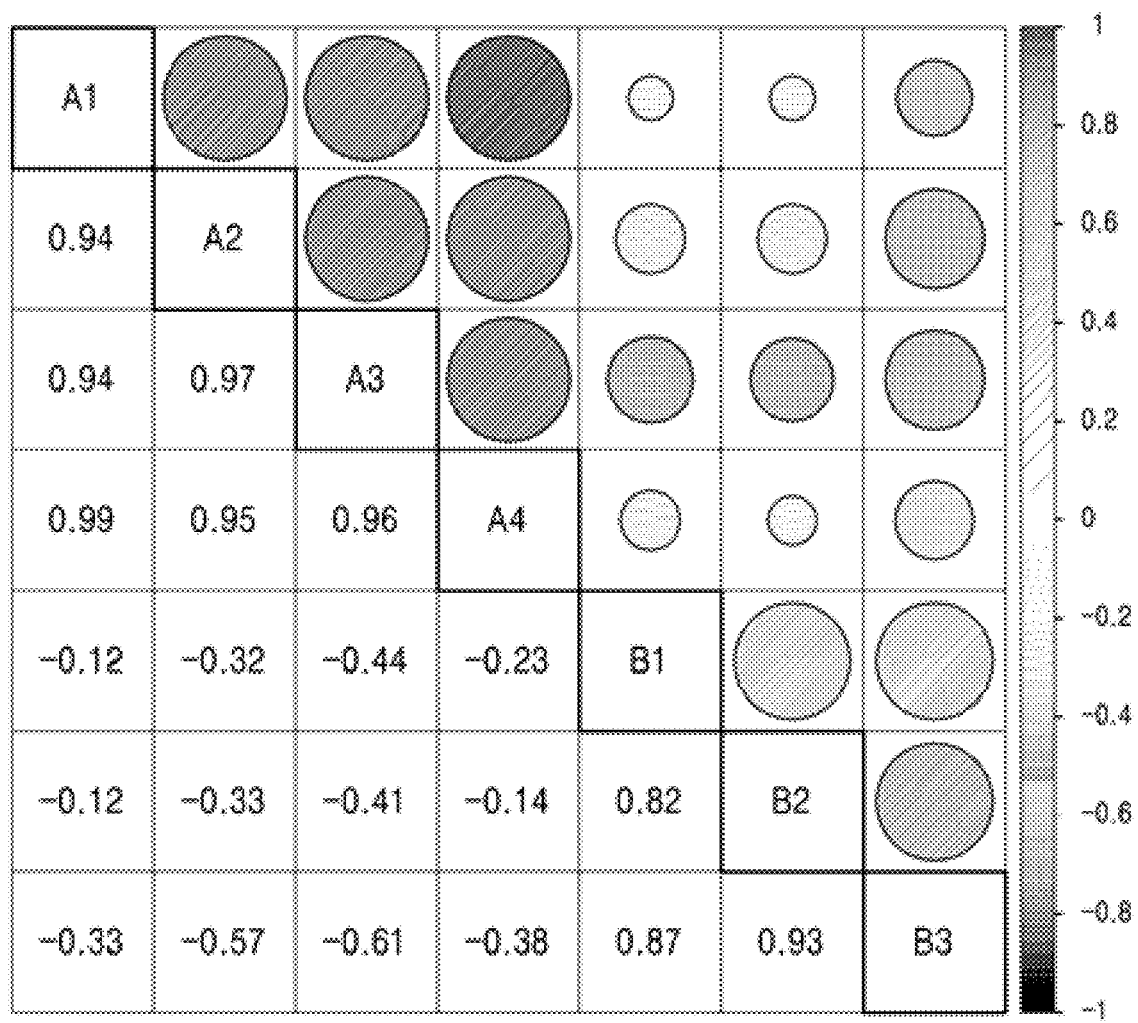
FIG. 7 is a diagram illustrating the reproducibility of the PMAS technique of the present disclosure.

As a result, the results of PMAS analysis on the feces samples collected from the same person showed a considerably similar trend (correlation coefficient of 0.8 or more) but differences from the results of PMAS analysis on the feces samples collected from the different person (FIG. 7). According to the above-described results, it can be seen that the result of analysis using the PMAS technique of the present disclosure is reproduced in the samples of the same person even under in vitro conditions.

(2) Verification of Identity with Clinical Result

To verify whether the result of analysis using the PMAS technique of the present disclosure shows identity with an actual clinical result, a test was performed as follows.

Specifically, feces samples were obtained from twenty four persons, and whether the content of short-chain fatty acids in the feces samples increased or decreased by treatment with probiotics A was analyzed using the PMAS technique of the present disclosure.

Then, after the same twenty four persons actually took the probiotics A, whether the content of short-chain fatty acids changed between feces samples obtained before and after intake was clinically checked, and the clinical result was compared with the result obtained by the PMAS technique (hereinafter, referred to as "PMAS result").

Figure 8:
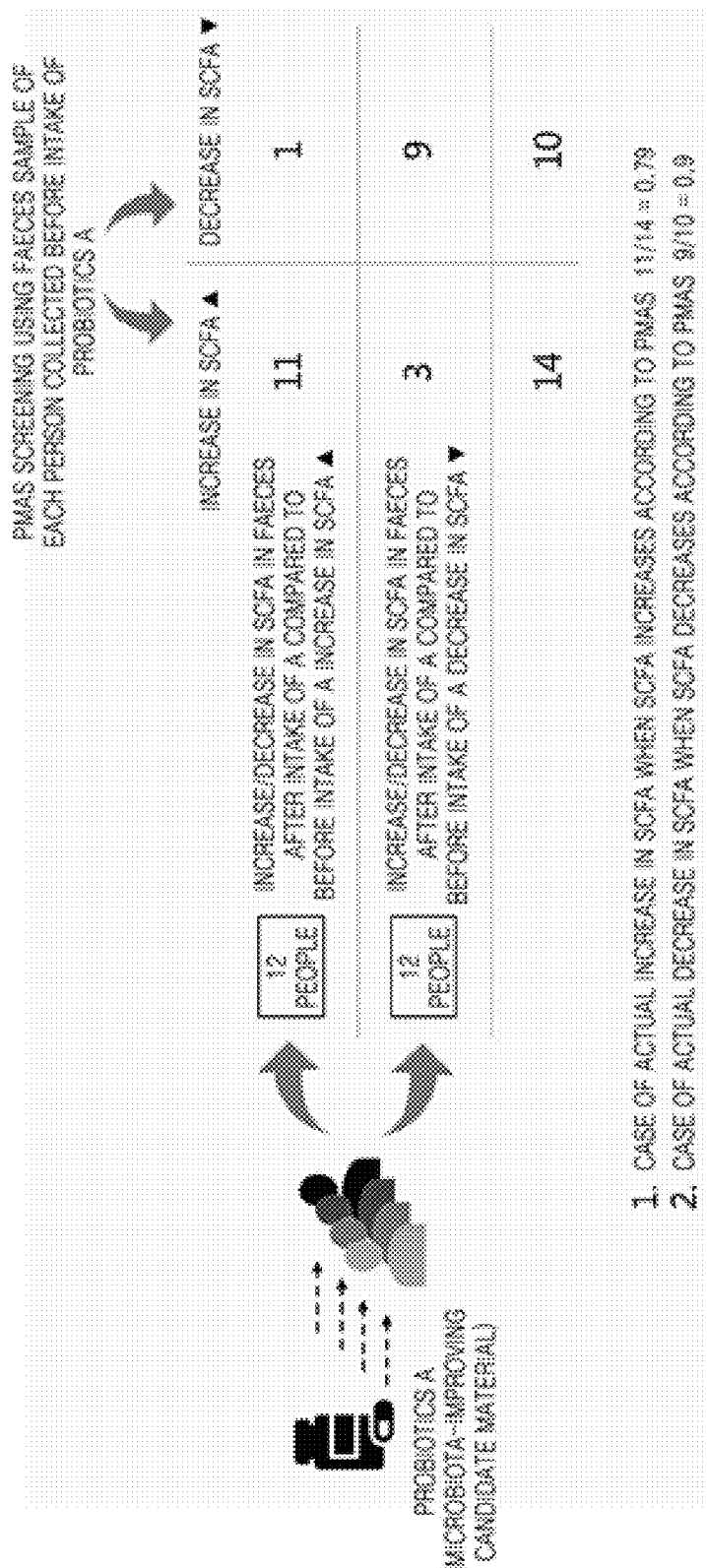
FIG. 8 is a diagram illustrating the identity between a clinical result and a result obtained by the PMAS technique of the present disclosure.

As a result, it was actually verified that twelve out of twelve persons showed an increase in short-chain fatty acids in their feces after intake of the probiotics A and the other twelve persons showed a decrease in short-chain fatty acids. Also, according to the result of verifying the effects of the probiotics A using the PMAS technique, short-chain fatty acids increased in the samples from a total of fourteen persons and decreased in the samples from ten persons (FIG. 8). Analysis was performed based on the above-described results as follows.

1) Cases of an actual increase in short-chain fatty acids when short-chain fatty acids increased according to the PMAS result—11/14=0.79

2) Cases of an actual decrease in short-chain fatty acids when short-chain fatty acids decreased according to the PMAS result—9/10=0.9

3) Cases of an increase in short-chain fatty acids according to the PMAS result among the persons whose short-chain fatty acids actually increased—11/12=0.92

4) Cases of a decrease in short-chain fatty acids according to the PMAS result among the persons whose short-chain fatty acids actually decreased—9/12=0.75

5) False negative to an increase in short-chain fatty acids—1-0.92=0.08

6) False positive to an increase in short-chain fatty acids—1-0.75=0.25

7) Assuming prevalence (frequency at which short-chain fatty acids increase after actual intake of the probiotics A) is 0.5, PPV=(0.92×0.5)/(0.92×0.5+(1−0.75)×(1−0.5))=0.79

According to the above-described results, the PMAS technique of the present disclosure makes it possible to achieve the reproducibility in the same subject even under in vitro conditions and obtain a result very similar to an actual clinical result. Therefore, it can be seen that the PMAS technique can mimic the intestinal environment very similarly and by using the PMAS technique, it is possible to rapidly and efficiently screen an intestinal environment-improving material very effective for each individual.

Test Example 4. Specific Embodiment of Personalized Material Candidate Screening System Using PMAS Technique By using the PMAS technique described above in Examples 1 to 3 and Test Examples 1 to 3, it is possible to rapidly and accurately analyze an individual's intestinal environment under in vitro conditions as described below and based on the result of analysis, it is possible to screen a candidate material capable of improving the intestinal environment. The following description is an example of a screening system using the PMAS technique, and it would be understood by a person with ordinary skill in the art that various changes and modifications can be made from the above description. For example, suitable results may be achieved if the described techniques are performed in a different order and/or if components in the described system, architecture, device, or process are combined in a different manner or replaced or substituted by other components or their equivalent.

(1) Preparation of Feces-Medium Mixture and Material Candidate Treatment

Figure 9:
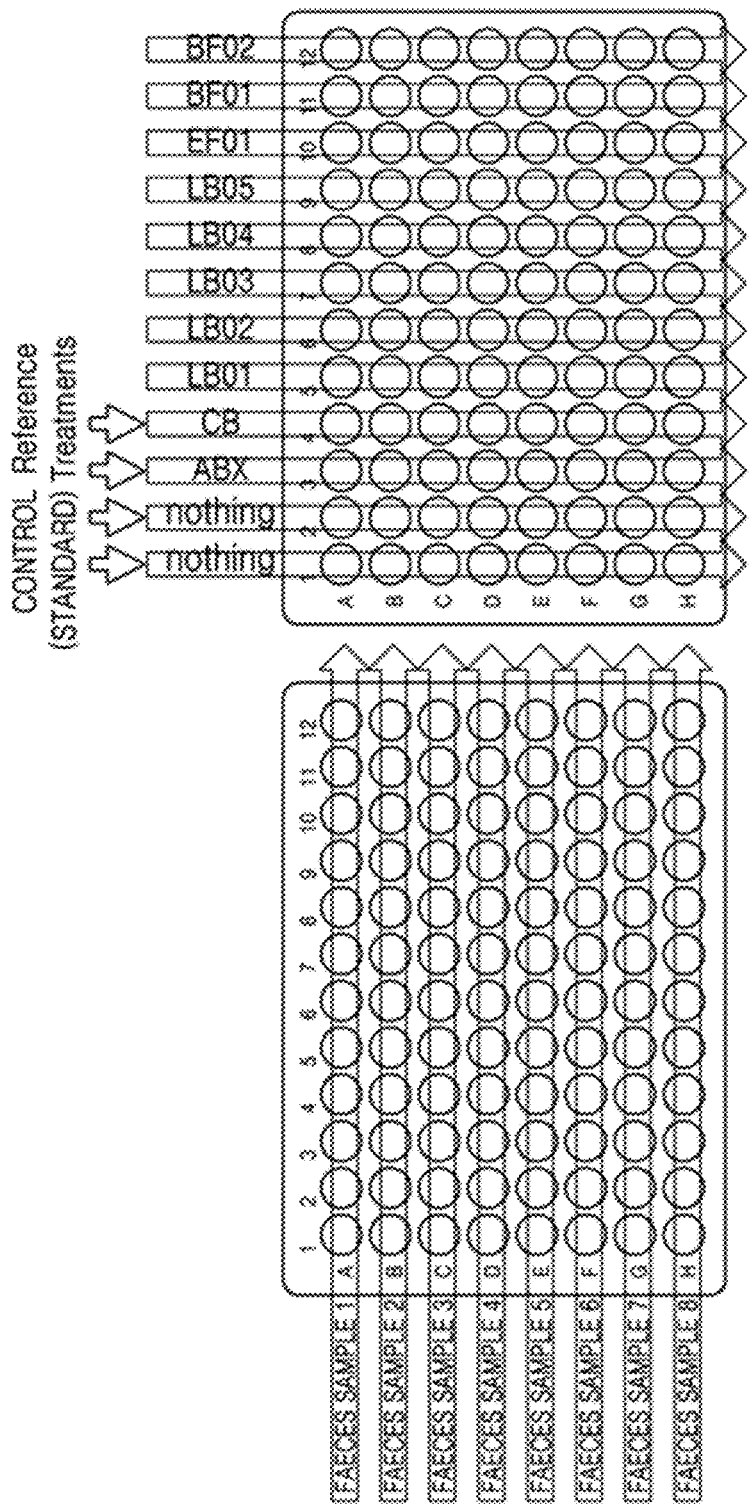
FIG. 9 is an exemplary diagram illustrating the configuration of a plate well when PMAS of the present disclosure is performed.

Each of feces samples obtained from eight persons was mixed with a PMAS medium and homogenized and then the same amount of the homogenized feces-medium mixture was dispensed to each of 96-well plates (horizontal axis), and the 96-well plates to which the feces samples were dispensed were vertically treated with different candidate materials (FIG. 9).

The control group (reference) was prepared to determine the degree of improvement in the intestinal environment by comparing analysis values measured after a PMAS test. An antibiotic mixture (ABX) in the reference treatment was used as a negative control group for creating an environment where microbial activities in feces sharply decreases and *Clostridium butyricum* (CB, bacterial strains that autonomously produce butyrate) was used as a positive control group for creating an environment where butyrate influential in determining whether the intestinal environment has been improved increases apparently. Also, other bacterial strains LB, EF, BF are candidate materials to be tested, and different numbers represent bacterial strains.

(2) PMAS Analysis Result—Analysis on Change in Amount of Butyrate

A PMAS test was performed using feces samples obtained from 100 adult persons in the same manner as described above in paragraph (1), and a change in amount of butyrate was analyzed. The result of analysis was as shown in FIG. 10.

Figure 10:
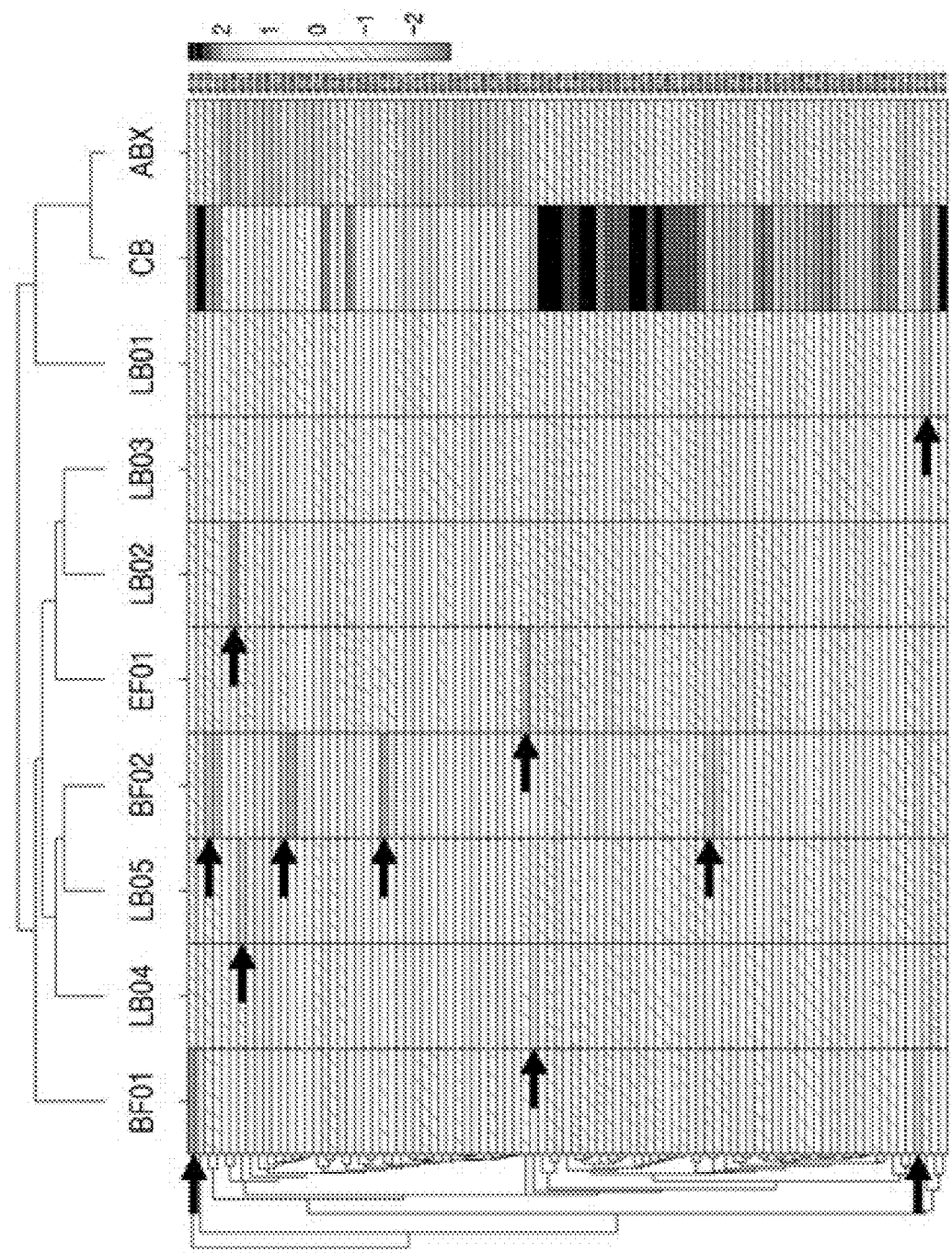
FIG. 10 is an exemplary diagram illustrating an analysis on a change in the amount of butyrate in a PMAS test of the present disclosure.

Specifically, each row in the heat map of FIG. 10 represents a feces sample, and dot represents the case of an increase and diagonal line represents the case of a decrease in amount of butyrate relative to a well of the control group (reference) after the execution of PMAS.

As a result, it can be seen that butyrate increases significantly in the case of treatment with CB which is a butyrate positive control group as compared with other treatments and butyrate decreases significantly in the case of treatment with ABX which is a negative control group as compared with other treatments (a decrease in microbial metabolite-butyrate caused by a decrease in microbial activities).

Further, candidate materials serving as test groups are *Lactobacillus*, Bifidobacteria, *Enterococcus*-based bacteria that cannot autonomously produce butyrate. However, it can be seen that some feces treated with such strains show an increase in butyrate (black arrow of FIG. 10). Accordingly, in some cases (some feces samples), it can be inferred that treatment with a specific candidate material in the PMAS environment induces a change in activity of other microorganisms in the samples (an increase in butyrate).

According to the above-described results, it can be seen that an environmental change caused by treatment with a candidate material in the PMAS technique is different for each feces sample. Accordingly, it can be seen that it is possible to screen an intestinal environment-improving candidate material based on microorganisms in each feces sample.

(3) PMAS Analysis Result—Change in Intestinal Microbial Diversity

A PMAS test was performed using feces samples obtained from 100 adult persons in the same manner as described above in paragraph (1), and a change in intestinal microbial diversity in some of the samples was analyzed. The result of analysis was as shown in FIG. 11.

Figure 11:
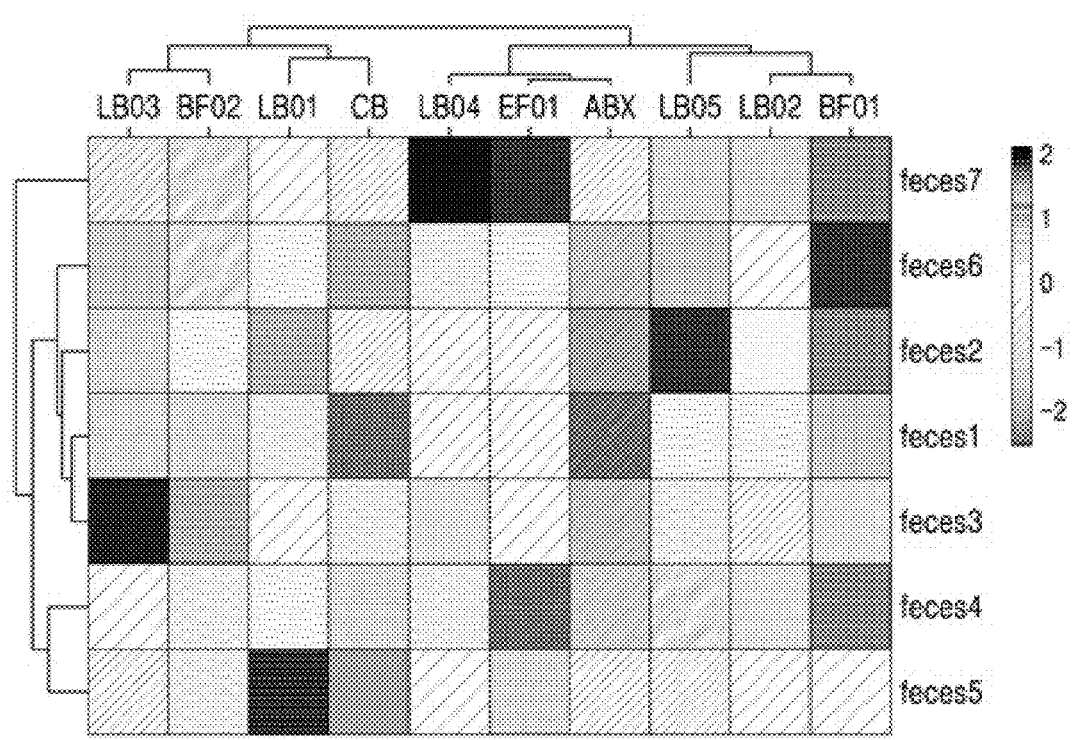
FIG. 11 is an exemplary diagram illustrating an analysis on a change in microbial diversity in a PMAS test of the present disclosure.

Specifically, each row in the heat map of FIG. 11 represents a feces sample, and dot represents the case of an increase and diagonal line represents the case of a decrease in microbial diversity relative to a well of the control group (reference) after the execution of PMAS.

As a result, it can be seen that a candidate material for increasing or decreasing the microbial diversity is different for each feces sample. Further, it was verified that an effect of each candidate material is expressed differently for each feces sample. Furthermore, it was verified that the microbial diversity decreases significantly in the case of treatment with ABX as compared with other treatment groups.

(4) PMAS Analysis Result—Correlation Between Microbial Composition of Initial Feces Sample and Change in Amount of Butyrate after PMAS Test A PMAS test was performed using feces samples obtained from 100 adult persons in the same manner as described above in paragraph (1), and a correlation between microbial composition and a change in amount of butyrate after the PMAS test was analyzed. The result of analysis was as shown in FIG. 12A and FIG. 12B.

Figure 12A:
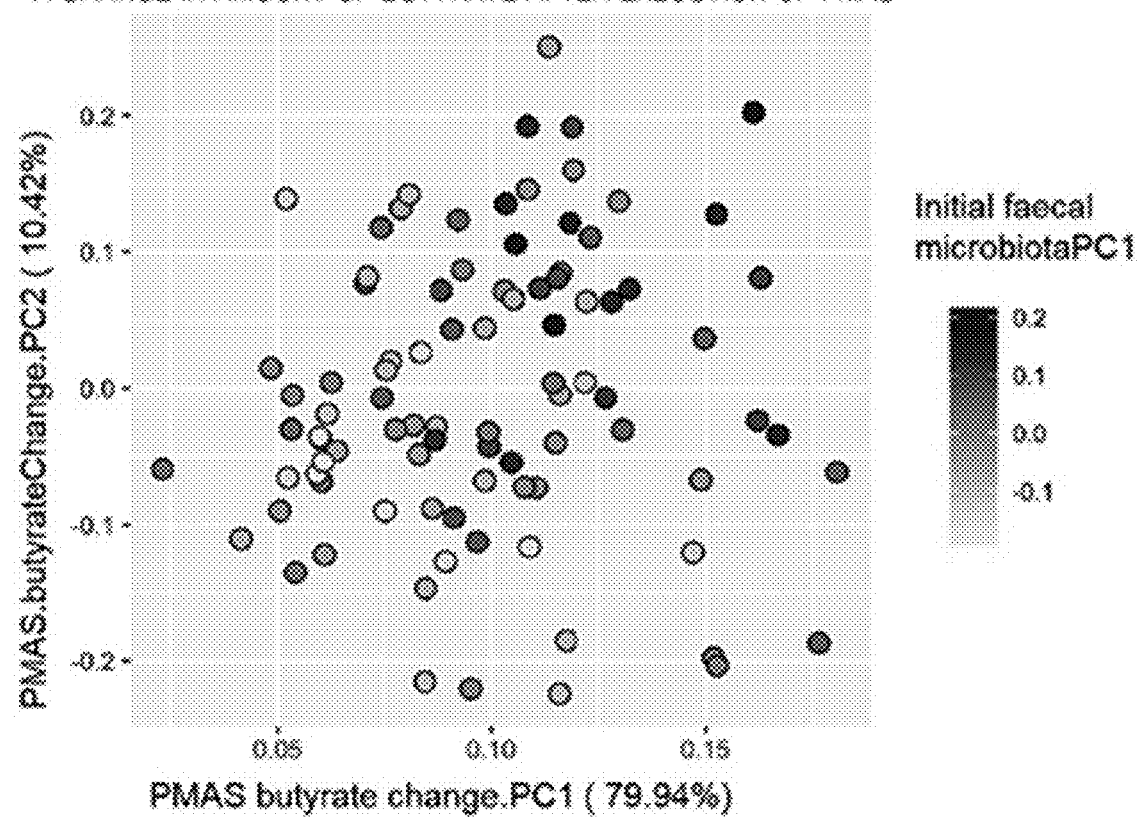
FIG. 12A and FIG. 12B are exemplary diagrams illustrating analysis on a correlation between microbial composition and butyrate.
Figure 12B:
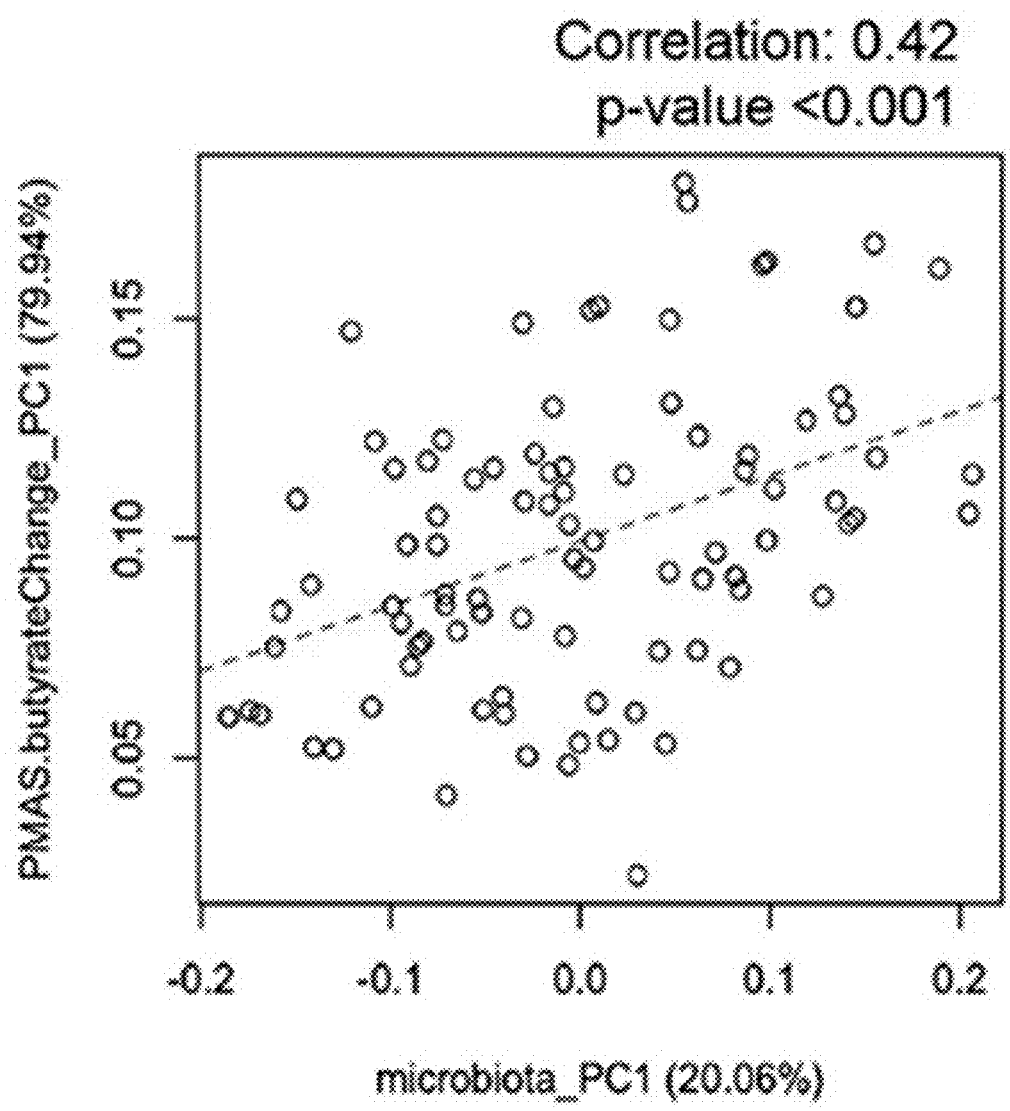

Specifically, FIG. 12A is a graph showing the results of change in butyrate in the feces samples treated with different candidate materials after the execution of PMAS (multivariate, ten results expect the reference control group) on the plane through PCA analysis (x-axis: PC1, y-axis: PC2, 90.36% of all data are represented and dots in the graph represent the respective feces samples) and the initial faecal microbiota PC1 in the category is a PC1 score obtained by expressing initial faecal microbiota in the feces before the execution of PMAS calculated in weighted UniFrac distance. Further, FIG. 12B is a graph showing a correlation between PC1 that is a main component of the results of change in butyrate in the respective feces samples after the execution of PMAS and PC1 that is beta diversity of microbiota change in the respective feces samples before the execution of PMAS.

According to the above-described results, it can be seen that "the results of change in butyrate in the respective feces samples after the execution of PMAS" has a significant correlation with "the results of microbial analysis before the execution of PMAS". That is, it can be inferred that a different pattern of change in butyrate for each feces sample after the execution of PMAS is caused by the distribution and composition of different microorganisms present in each feces sample (the change in butyrate is not random).

The above description of the present disclosure is provided for the purpose of illustration, and it would be understood by a person with ordinary skill in the art that various changes and modifications may be made without changing technical conception and essential features of the present disclosure. Thus, it is clear that the above-described examples are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

The invention claimed is:

1. A method for screening an intestinal environment-improving material, comprising:
   (a) mixing a composition for screening an intestinal environment-improving material with a sample obtained from a subject;
   (b) treating the mixture from step (a) with one or more intestinal environment-improving candidate materials and culturing the mixture; and
   (c) analyzing the culture from step (b) to analyze toxin, intestinal microbiota, microbiota-derived metabolite, or a mixture thereof in the culture to determine content or concentration thereof,
   wherein
   the intestinal environment-improving material is selected from the group consisting of probiotic, prebiotic, food, health functional food, drug and a mixture thereof;
   the composition for screening an intestinal environment-improving material does not include protein and carbohydrate; and
   the toxin is endotoxin or hydrogen sulfide.

2. The method of claim 1, wherein the composition for screening an intestinal environment-improving material comprises L-cysteine.

3. The method of claim 1, wherein the composition for screening an intestinal environment-improving material comprises L-cysteine and mucin.

4. The method of claim 1, wherein the microbiota-derived metabolite is a short-chain fatty acid (SCFA).

5. The method of claim 4, wherein the short-chain fatty acid is selected from the group consisting of acetate, propionate, butyrate, isobutyrate, valerate and iso-valerate.

6. The method of claim 1, wherein the method is performed under in vitro conditions.

7. The method of claim 1, wherein the culturing in step (b) is performed under an anaerobic condition for 18 hours to 24 hours.

8. The method of claim 1, wherein the analyzing the culture in the step (c) is to analyze the content, concentration, or type of toxin.

9. The method of claim 1, wherein the analyzing the culture in the step (c) is to analyze the kind, concentrate, content or diversity change of intestinal microbiota contained in the culture.

10. A method for screening an intestinal environment-improving material of claim 1, further comprising:
    (d) screening a candidate material that increases the content of the short-chain fatty acids, increases the kind and content of beneficial bacteria in the microbiota, decreases the contents of endotoxin and hydrogen sulfide or decreases the kind and content of harmful bacteria in the microbiota by comparison between the result of analysis from the step (c) and the result of analysis on a control group.

11. A method for screening an intestinal environment-improving material, comprising:
    (1) preparing a mixture of human or animal feces and a Pharmaceutical Meta-Analysis Screening (PMAS) medium by the steps of:
        (a) obtaining feces of a human or animal and mixing the feces with a PMAS medium,
        (b) homogenizing the mixture using a stomacher;
        (c) filtering fecal residues from the feces;
        (d) reducing the feces-medium mixture in an anaerobic chamber for 4 hours,
    (2) Dispensing identical quantities of the feces-PMAS medium mixture into culture plates in an anaerobic chamber;
    (3) screening each candidate intestinal environment-improving material by the steps of:
        (i) suspending each of the candidate materials in sterile 1×PBS;
        (ii) homogenizing each of the candidate materials and then dispensing the homogenized candidate materials to the respective plates prepared in Step (2) where the feces-medium mixture was placed,
    (4) culturing the prepared plates under anaerobic conditions with temperature, humidity and motion similar to those of the intestinal environment to ferment and culture the respective test groups; and
    (5) centrifuging the culture products of step (4) to obtain supernatant; and
    (6) testing for the presence of toxic or undesirable substances comprising hydrogen sulfide, bacterial LPS, short-chain fatty acids in the supernatant, and/or undesirable microbiota; and identifying those intestinal environment-improving material wherein the corresponding cultured sample results in reduced levels of toxic or undesirable substances relative to a control fecal sample not treated with a candidate an intestinal environment-improving material.

12. The method of claim 11 wherein the feces and the PMAS medium are mixed in a ratio of 1:12.

13. The method of claim 11 wherein the PMAS medium comprises glucose, tryptone, mucin or L-cysteine hydrochloride.

* * * * *